United States Patent
Liu et al.

(10) Patent No.: US 10,823,858 B2
(45) Date of Patent: Nov. 3, 2020

(54) HYBRID X-RAY DETECTOR STRUCTURE

(71) Applicant: General Electric Company, Schenectady, NY (US)

(72) Inventors: James Liu, Salt Lake City, UT (US); Nicholas Konkle, Waukesha, WI (US); Biju Jacob, Niskayuna, NY (US); Douglas Albagli, Clifton Park, NY (US); William Hennessy, Troy, NY (US); Habib Vafi, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 443 days.

(21) Appl. No.: 15/881,221

(22) Filed: Jan. 26, 2018

(65) Prior Publication Data

US 2019/0235097 A1    Aug. 1, 2019

(51) Int. Cl.

| | |
|---|---|
| *G01T 1/24* | (2006.01) |
| *H01L 27/146* | (2006.01) |
| *A61B 6/06* | (2006.01) |
| *G01T 1/20* | (2006.01) |
| *A61B 6/00* | (2006.01) |
| *A61B 6/10* | (2006.01) |

(52) U.S. Cl.
CPC ............ *G01T 1/244* (2013.01); *A61B 6/06* (2013.01); *A61B 6/107* (2013.01); *A61B 6/4208* (2013.01); *A61B 6/4441* (2013.01); *A61B 6/563* (2013.01); *G01T 1/20* (2013.01); *G01T 1/2018* (2013.01); *H01L 27/14618* (2013.01); *H01L 27/14623* (2013.01); *H01L 27/14625* (2013.01); *H01L 27/14661* (2013.01); *H01L 27/14663* (2013.01); *H01L 27/14685* (2013.01); *H01L 27/14689* (2013.01)

(58) Field of Classification Search
CPC ......... G01T 1/244; G01T 1/20; G01T 1/2018; H01L 27/14689; H01L 27/14685; H01L 27/14618; H01L 27/14625; H01L 27/14623; H01L 27/14661; H01L 27/14663; A61B 6/107; A61B 6/563; A61B 6/4441; A61B 6/4208; A61B 6/06; A61B 6/4233
See application file for complete search history.

(56) References Cited

U.S. PATENT DOCUMENTS

| | | | |
|---|---|---|---|
| 9,513,383 B1 * | 12/2016 | Cao | .................. G01T 1/2018 |
| 2017/0229502 A1 | 8/2017 | Liu et al. | |
| 2017/0294033 A1 * | 10/2017 | Ganguly | ............... G06T 11/008 |
| 2018/0024253 A1 * | 1/2018 | Jacobs | ................. A61B 6/4417 |
| | | | 378/62 |

* cited by examiner

*Primary Examiner* — David P Porta
*Assistant Examiner* — Meenakshi S Sahu
(74) *Attorney, Agent, or Firm* — Boyle Fredrickson, S.C.

(57) ABSTRACT

An imager panel for an x-ray detector for obtaining x-ray images of an object is provided that includes a first portion disposed at the center of the hybrid imager panel that can produce images of a first resolution and a second portion disposed at least partially around the first portion that is capable of producing images of a second resolution. The hybrid imager panel provides a hybrid detector that can be selectively operated to obtain images of varying resolutions corresponding to the first resolution from the first portion, the second resolution from the second portion or a combination thereof.

20 Claims, 7 Drawing Sheets

HYBRID X-RAY DETECTOR STRUCTURE

BACKGROUND OF THE DISCLOSURE

In order to obtain X-ray images of interior structures of a body, such as a piece of luggage or the body of a patient, various types of imaging systems are employed. In many prior art imaging systems, the detector is formed as a separable component form the remainder of the imaging system. The detector is formed as a structure with a housing enclosing the components of the detector necessary to detect the impingement of X-rays thereon to form the X-ray image.

In many detector structures for direct or indirect flat panel detectors, the enclosure includes a rigid back cover secured to a front cover of the enclosure. The enclosure contains various components for enabling the detector to function as desired, including an imager that is struck by the X-rays, different electronic components for receiving data from the imager, a backscatter shield, a scintillator and photodiode for indirect detector structures, and a power source for supplying power to the various components of the detector.

The imager panel of the detector is normally formed from either an amorphous silicon (a-Si) material or a complementary metal oxide semiconductor material (CMOS). Each material is capable of generating electrical signals representative of the x-rays or light striking the panel in order to form the digital images of the object, such as a patient, through which the x-rays pass.

While both materials are capable of functioning as the imager panel, the CMOS panel has significant advantages over the amorphous silicon (a-Si) panel in low dose applications. First, the CMOS panel has a lower electronic noise and a better electromagnetic interference (EMI) immunity than an a-Si panel. Next, the CMOS panel has a lower static power consumption and lower lag and faster frame rate than an a-Si panel. Also, the pixel size for the CMOS panel can be significantly smaller than that of the a-Si panel, with a resulting increase in spatial resolution of the images produced by the CMOS panel.

However, while a CMOS panel has these and additional advantages over an a-Si panel, the CMOS panel is also much more expensive to construct, which limits its applicability. For example, while the CMOS panel can be cost effectively utilized in smaller detector constructions, i.e., 6 inch detectors, the cost of the CMOS panel significantly limits its usage in larger detectors, i.e. 12 inch detectors. As a result, the requirement for the use of a-Si panels in larger detectors greatly reduces the resolution that can be achieved in the resulting images, among other issues.

Accordingly, it is desirable to provide a detector for an X-ray imaging system capable of producing improved images, such as images with increased resolution and/or higher frame rate, from a large imager panel without significantly increasing the costs for the imager panel.

BRIEF DESCRIPTION OF THE DISCLOSURE

There is a need or desire for an x-ray detector that is capable of producing higher performance images from a hybrid imager panel having imager panel components capable of providing images of different noises, read out rates and/or resolutions. According to one exemplary aspect of the disclosure, the hybrid imager panel includes a first section disposed at the center of the hybrid imager panel that can produce images of a first noise, read out rate and/or resolution and a second portion disposed at least partially around the first portion that is capable of producing images of a second noise, read out rate and/or resolution. The hybrid imager panel provides a hybrid detector that can be selectively operated to obtain images of varying noises and/or resolutions corresponding to the first noise and/or resolution from the first portion, the second noise and/or resolution from the second portion or a combination thereof.

According to another exemplary aspect of the disclosure, hybrid imager panel is formed by initially providing an imager panel formed of the second portion and forming a space for the placement of the first portion in relation to the second portion to form the hybrid imager panel. The detector including the hybrid imager panel can be operated in a number of different manners in order to provide images of the object being scanned having the desired performance and/or resolution.

According to a further exemplary aspect of the disclosure, a hybrid imager panel for an x-ray detector includes a first portion including a first imaging panel having a first image resolution and a second portion at least partially surrounding the first portion and including a second imaging panel having a second image resolution, wherein the first image resolution is different that the second image resolution.

According to still a further aspect of the disclosure, a detector for use in conjunction with an X-ray imaging system includes an enclosure, a hybrid imager panel disposed within the enclosure and having a second imaging panel formed of a second material and including an aperture in the second imaging panel and a first imaging panel formed of a first material and disposed at least partially within the aperture, wherein the first material is different than the second material, and an electronics layer operably connected to the first portion and the second portion of the hybrid imager panel.

According to still another aspect of the disclosure, a method for forming a hybrid imager panel for a detector for use in conjunction with an X-ray imaging system includes the steps of forming a second imaging panel formed of a second material, forming an aperture in the second imaging panel and positioning a first imaging panel formed of a first material at least partially within the aperture, wherein the first material is different than the second material.

According to still a further aspect of the disclosure, a method of operating a detector for use in conjunction with an X-ray imaging system including a hybrid imager panel includes the steps of providing the detector including the hybrid imager panel having a first portion including a first imaging panel having a first image resolution and a second portion at least partially surrounding the first portion and including a second imaging panel having a second image resolution, wherein the first image resolution is different from the second image resolution, selecting a magnification configuration for the hybrid imager panel and operating the hybrid imager panel in the selected magnification configuration.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The drawings illustrate the best mode presently contemplated of carrying out the disclosure, in the drawings.

DETAILED DESCRIPTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

One or more specific implementations will be described below. In an effort to provide a concise description of these implementations, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements.

While the following discussion is generally provided in the context of medical imaging, it should be appreciated that the present techniques are not limited to such medical contexts. Indeed, any examples and explanations provided in such a medical context is only to facilitate explanation by providing instances of real-world implementations and applications. However, the present approaches may also be utilized in other contexts, such as the non-destructive inspection of manufactured parts or goods (i.e., quality control or quality review applications), and/or the non-invasive inspection of packages, boxes, luggage, and so forth (i.e., security or screening applications).

Figure 1:
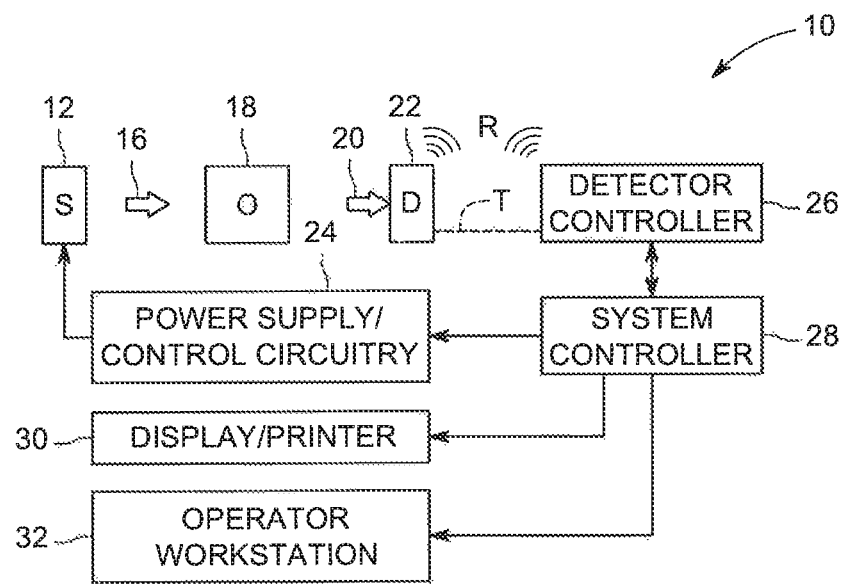
FIG. 1 is a schematic representation of a digital X-ray imaging system, according to an exemplary non-limiting embodiment of the invention.

FIG. 1 illustrates diagrammatically an imaging system 10 for acquiring and processing image data using a detector fabricated and/or operated as discussed herein, such as that disclosed in US Patent Application Publication No. 2017/0229502, entitled Active Pixel Radiation Detector Array And Use Thereof, which is expressly incorporated herein by reference in its entirety for all purposes. In the illustrated embodiment, system 10 is a digital X-ray system designed both to acquire original image data and to process the image data for display. The imaging system 10 may be a stationary or mobile X-ray system. In the embodiment illustrated in FIG. 1, imaging system 10 includes a source of X-ray radiation 12 that emits a stream of radiation 16 into a region in which an object or subject 18 is positioned. The X-ray radiation source 12 is controlled by a power supply/control circuit 24 which furnishes both power and control signals for examination sequences. A portion of the radiation 20 passes through or around the subject and impacts a digital X-ray detector, represented generally at reference numeral 22. The detector 22 may be portable or permanently mounted to the system 10. In certain embodiments, the detector 22 may convert the incident X-ray photons to lower energy photons which are detected. Electrical signals are generated in response to the detected photons and these signals are processed to reconstruct an image of the features within the object or subject.

As discussed herein, the detector array 22 may include one or more CMOS light imager panels, each separately defining an array of detector elements (e.g., active pixels). Each detector element produces an electrical signal that represents the intensity of the X-ray beam incident at the position of the detector element when the beam strikes the detector 22. In the depicted example, the detector 22 includes or communicates with a detector controller 26 (e.g., control circuitry) which commands acquisition of the signals generated in the detector 22. In the presently illustrated embodiment, the detector 22 may communicate with the detector controller 26 via any suitable wireless communication standard (R), although the use of digital X-ray detectors 22 that communicate with the detector controller 26 through a cable (T) or some other mechanical connection are also envisaged. Alternatively, operational aspects of the detector controller 26 may be implemented on, or otherwise provided of, the detector 22 itself in some implementations. Detector controller 26 may also execute various signal processing and filtration functions, such as for initial adjustment of dynamic ranges, interleaving of digital image data, and so forth.

Both power supply/control circuit 24 and detector controller 26 are responsive to signals from a system controller 28. In general, system controller 28 commands operation of the imaging system to execute examination protocols and to process acquired image data. In the present context, system controller 28 may also include signal processing circuitry and one or more data storage structures, such as optical memory devices, magnetic memory devices, or solid-state memory devices, for storing programs and routines executed by a processor of the system 10 to carry out various functionalities, as well as for storing configuration parameters and image data. In one embodiment, a programmed computer system may be provided with hardware, circuitry, firmware, and/or software for performing the functions attributed to one or more of the power supply/control circuit 24, the detector controller 26, and/or the system controller 28.

In the embodiment illustrated in FIG. 1, system controller 28 is linked to at least one output device, such as a display or printer as indicated at reference numeral 30. The output device may include standard or special purpose monitors and associated processing circuitry. One or more operator workstations 32 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, cloud-based network, and so forth.

The X-ray system 10 as shown in FIG. 1 may also include a variety of alternative embodiments generally configured to meet the particular needs of certain applications. For example, the X-ray system 10 may be either fixed, a mobile system, or a mobile C-arm system where the X-ray detector is either permanently mounted inside one end of the C-arm or removable from the system. Further, the X-ray system 10 may be a table and/or wall stand system in a fixed X-ray room where the X-ray detector 22, such as a flat panel detector including a direct or indirect flat panel detector or a cassette detector, is either permanently mounted together with the system or portable. Alternatively, the X-ray system 10 may be a mobile X-ray system with a portable X-ray detector. Such a portable X-ray detector may be further constructed with a detachable tether or cable used to connect the detector readout electronics to the data acquisition system of the scanner. When not in use, a portable X-ray detector may be detached from the scan station for storage or transfer. In practice, the imaging system 10 may be any suitable X-ray based imaging system, including, but not limited to, conventional radiography systems, CT imaging systems, tomosynthesis systems, C-arm systems, fluoroscopy systems, mammography systems, dual- or multiple-energy systems, navigational or interventional imaging systems, and so forth.

Figure 2:
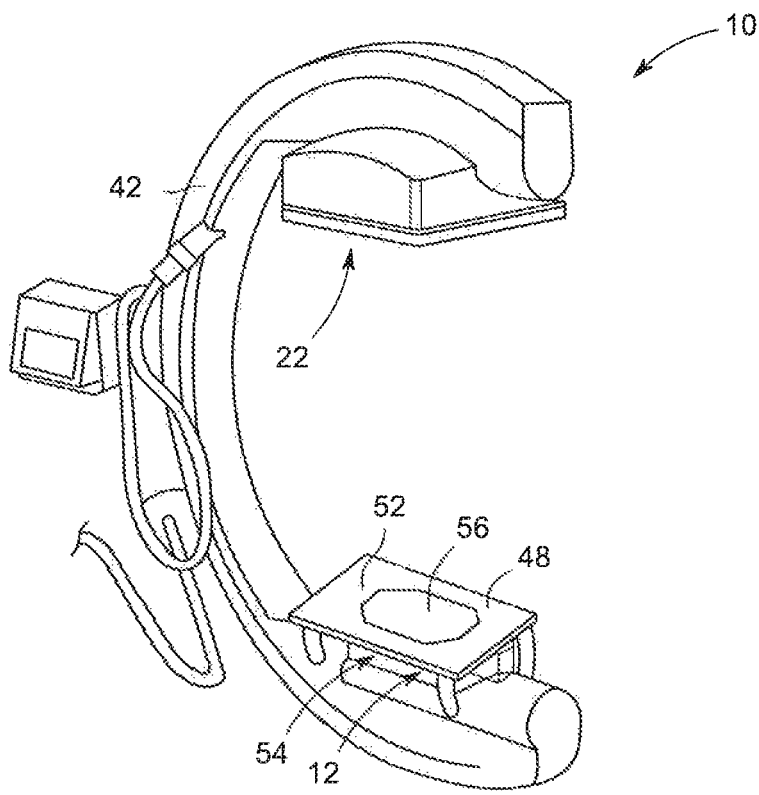
FIG. 2 is an isometric view of an X-ray imaging system according to an exemplary non-limiting embodiment of the invention.

While the preceding schematically describes components of an X-ray based imaging system 10, including a detector and detector control and readout circuitry as discussed herein, FIG. 2 depicts an example of how such an imaging system 10 may be provided in a real-world context. As noted above, the X-ray system 10 may be implemented as a mobile X-ray device (e.g., an X-ray device comprising a C-arm, a mini C-arm, an O-arm, a non-circular arm, and so forth), and a fixed X-ray device. By way of illustration, FIG. 2 shows an X-ray imaging system 10 that comprises a C-arm X-ray device 42 configured to rotate a detector panel 22 and X-ray source 12 about a volume to be imaged. In the depicted example, the X-ray system 10 also includes a collimator 48. Any suitable X-ray source 12 can be used, including a standard X-ray source, a rotating anode X-ray source, a stationary or fixed anode X-ray source, a solid state X-ray emission source, or a fluoroscopic X-ray source 54 (as shown in FIG. 2). Any suitable X-ray detector 22 can be used, including a digital detector as discussed in greater detail below.

FIG. 2 shows an implementation in which the collimator 48 comprises an X-ray attenuating material 52 that defines an aperture 56 through which X-ray may pass, and which in turn prevents or limits X-ray emission beyond the bound of the defined aperture, thus shaping and limiting the defined beam. The collimator 48 can comprise any suitable X-ray attenuating material 52 that allows it to collimate an X-ray beam in this manner. Some examples of suitable X-ray attenuating materials include tungsten, lead, gold, copper, tungsten-impregnated substrates (e.g., glass or a polymer impregnated with tungsten), coated substrates (e.g., glass or a polymer coated with tungsten, lead, gold, etc.), steel, aluminum, bronze, brass, rare earth metals, or combinations thereof.

Figure 3:
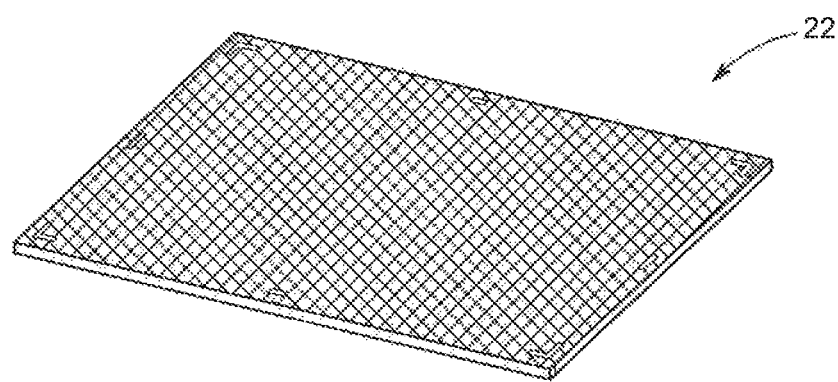
FIG. 3 is an isometric view of an x-ray detector cassette/enclosure according to an exemplary non-limiting embodiment of the invention.
Figure 4:
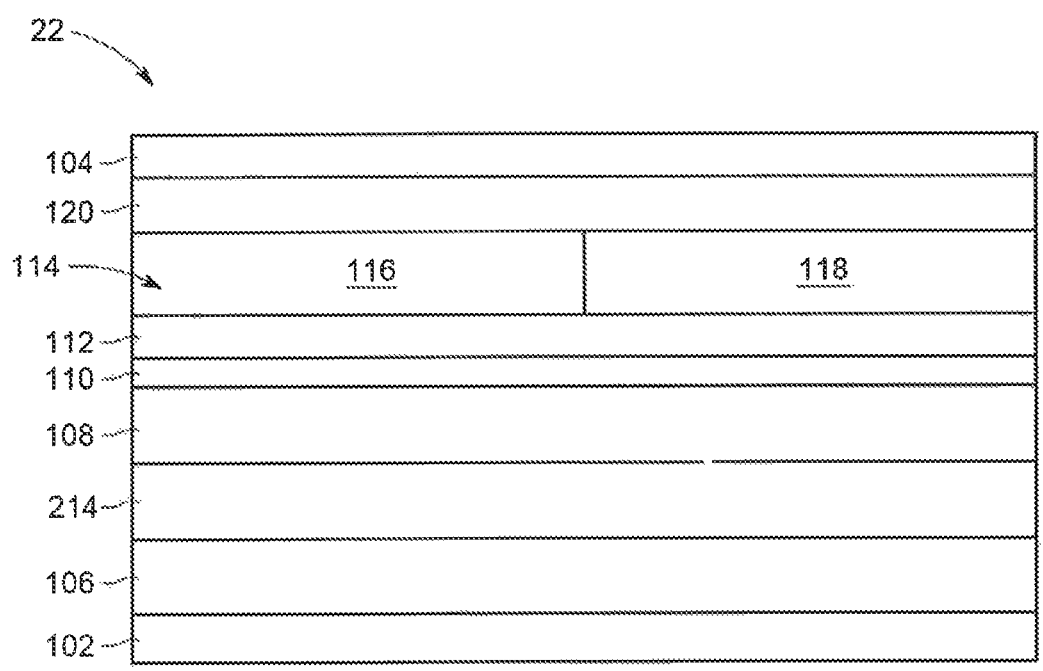
FIG. 4 is an exploded view of an x-ray detector cassette/enclosure according to an exemplary non-limiting embodiment of the invention.

Looking now at the exemplary illustrated embodiment shown in FIGS. 3-4, the detector 22 includes a housing or enclosure 100 formed with a front cover 102 and a rear cover 104. The front cover 102 and rear cover 104 are normally formed of a rigid and lightweight material on order to provide protection to the interior components of the detector 22 without significantly increasing the weight of the detector 22. In an exemplary embodiment, the front cover 102 is formed of a material that is transparent to x-rays, such as a carbon fiber material, while the rear cover 104 is formed from a metal, such as a lightweight magnesium-lithium alloy material.

Between the front cover 102 and rear cover 104 the interior components of the detector 22 include a foam layer 106,124 disposed immediately adjacent the front cover 102 and present to provide a separation layer between the rigid front cover 102 and an x-ray scintillator 214. An imager 108 is disposed adjacent the scintillator 214. The imager 108 is formed in a known manner of a material capable of detecting light photons generated by the x-ray scintillator 214 while x-rays striking the scintillator 214 in order to provide image data concerning the impingements of the x-rays upon the scintillator 214.

Adjacent the imager 108 but opposite the scintillator 214 is located a lead backscatter shield 110 present to capture any stray x-rays passing through or around the imager 108. The backscatter shield 110 is disposed on one side of a support layer 112. The support layer 112 provides internal structural support to the detector 104 and can be formed of a lightweight and rigid material, such as an MgLi alloy.

Opposite the shield 110, the support layer 112 provides an attachment point for the electronics 114 that are operably connected to the imager 108 and that control the operation of the detector 104. The electronics 114 can include digital electronics 116 and/or scan/data processing electronics 118 that are operably connected to the imager 108 and to one another, as well as to batteries 120 also disposed on the support layer 112. The rear cover 104 is secured to the front cover 102 and the support layer 112 adjacent the electronics 114 in order to provide the rigid enclosure 100 for and around the various components 106-120 within the detector 22.

Figure 5:
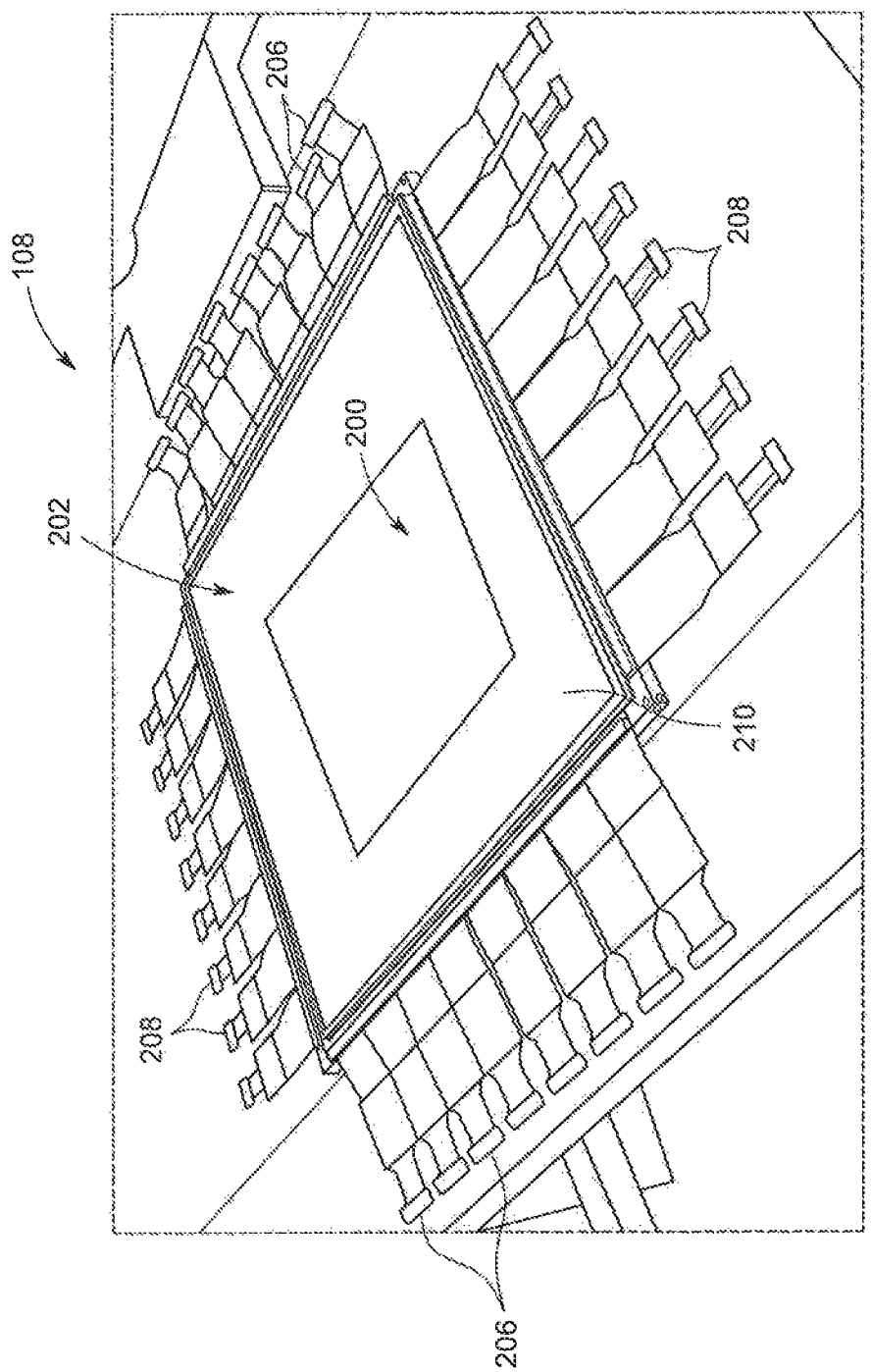
FIG. 5 is an isometric view of a hybrid imager panel of the detector according to an exemplary non-limiting embodiment of the invention.
Figure 6:
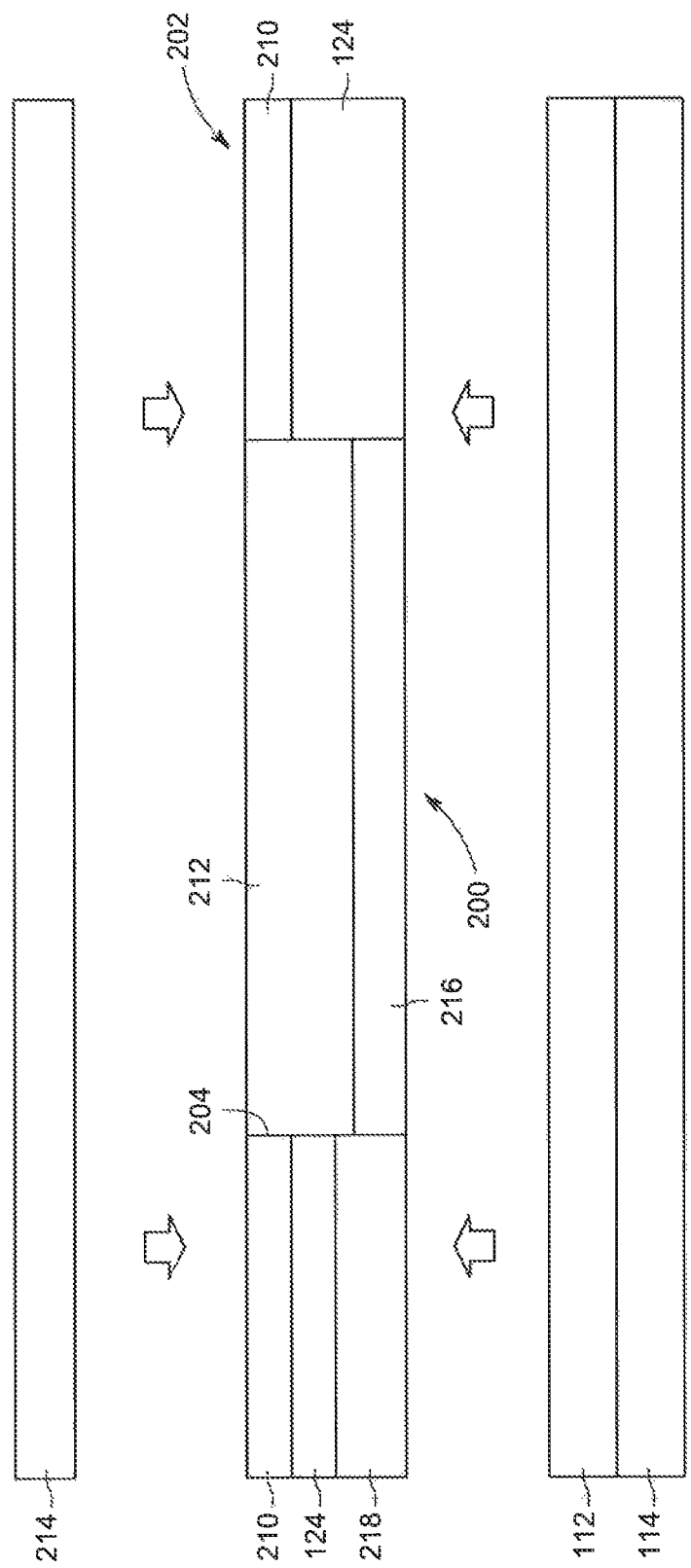
FIG. 6 is cross-sectional view of the hybrid imager panel of FIG. 5 constructed according to an exemplary non-limiting embodiment of the invention.
Figure 7:
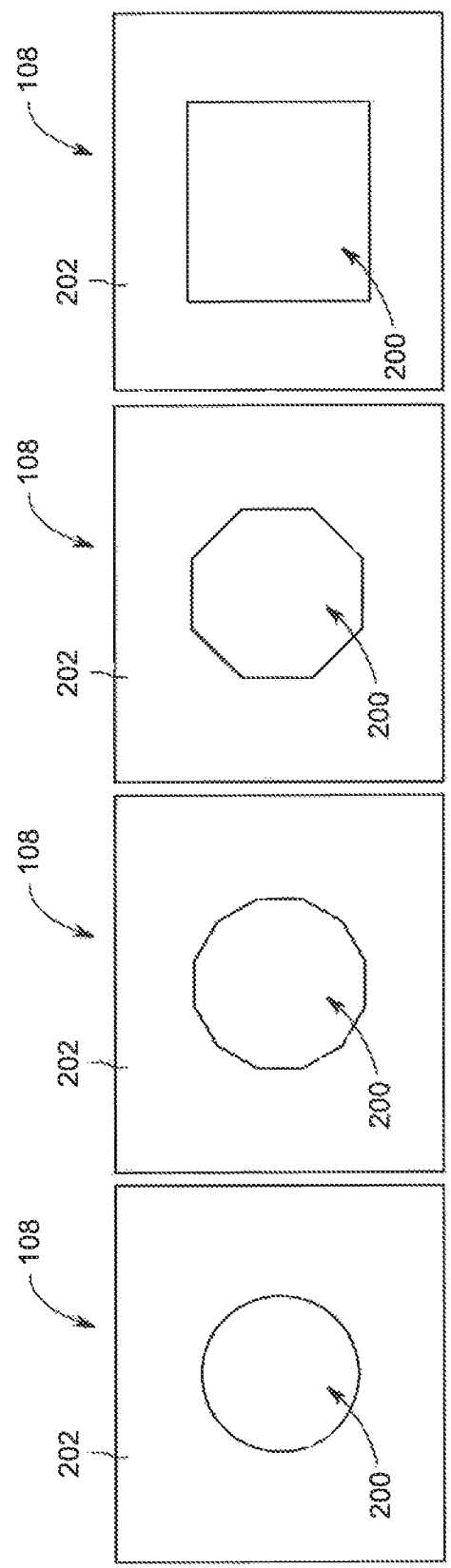
FIGS. 7A-7D are top plan views of various alternative configurations for the hybrid imager panel according to another exemplary non-limiting embodiment of the invention

Referring now to FIGS. 5 and 6, an exemplary embodiment of the imager or imager panel 108 is illustrated. The panel 108 is a hybrid panel including a first portion 200 and a second portion 202. The first portion 200 and the second portion 202 are capable of producing images of different resolutions when x-rays impinge upon the first portion 200 and the second portion 202. In the illustrated exemplary embodiment of FIGS. 4 and 5, the second portion 202 includes a central space, cut out or aperture 204 that conforms to the perimeter shape of the first portion 200.

In one exemplary embodiment, the first portion 200 is form of a CMOS panel while the second portion 202 is formed of an a-Si panel. In this configuration, the position of the CMOS first portion 200 at the center of the hybrid panel 108 enables the first portion 200 to provide the high frame rate, high resolution and low noise images for the portion of the object being scanned that is located at the center of the panel 108. As the central part of the imager panel 108 is normally aligned with the areas of most interest to the physician or other individual viewing the images provided by the panel 108, the central part of the panel 108 where the first portion 200 is located should be able to provide these high quality images. For example, the first portion 200 formed of the CMOS panel can provide a pixel size of 100 μm or less, or of 50 μm or less, as opposed to the second portion 202 formed of the a-Si panel, which has a pixel size of approximately 200 μm, 150 μm, or 100 μm.

In illustrated exemplary embodiment of FIG. 5, the panel 108 is illustrated as including the first portion 200 disposed centrally within the second portion 202 that surrounds the perimeter of the first portion 200. The second portion 202 is operably connected to the scan/data electronics 118 of electronics layer 114, which as shown constitutes separate pairs of scan modules 206 and data modules 208 attached to the hybrid panel 108 to provide double side scan and double side read capability for the panel 108. The scan modules 206 are operated to select what areas or pixels on the panel 108 to read while the data modules 208 obtain or read the data from the selected areas or pixels of the panel 108, with each set of corresponding scan modules 206 and data modules 208 configured to operate one half of the panel 108.

In the embodiment of FIG. 5 where the first portion 200 is disposed within the second portion 202, one set of scan modules 206 and one corresponding set of data modules 208 can be re-configured/connected to the first portion 200 in order to control the operation of the first portion 200 separate from the remaining set of scan modules 206 and data modules 208 which are operable to concurrently control the operation of the second portion 202. This construction reduces the complexity of the hybrid panel 108 by utilizing parts of the existing scan modules 206 and data modules 208 already present on the panel 108 and simply reconnecting them to the first portion 200 to control the operation of the first portion 200 separate from the second portion 202.

Looking now at FIG. 6, in one illustrated exemplary embodiment of the hybrid panel 108, the placement of the first portion 200 within the second portion 202 is defined by an aperture 204 that is cut through the second portion 202 into a shape conforming to the shape of the perimeter of the first portion 200. The aperture 204 is formed in the second portion 202 in any suitable manner, such as by cutting the aperture 204, e.g., laser cutting the aperture 204 in the second portion 202, or by initially forming the second portion 202 with the aperture 204 therein. In the illustrated exemplary embodiment the aperture 204 extends not only though the a-Si panel 210 of the second portion 202, but also through the foam layer 106, such that the aperture 204 extends entirely through the second portion 202.

After the aperture 204 has been formed, a fiber optic plate (FOP) 212 formed of a material that does not distort or otherwise negatively affect the resolution of the images provided by the first portion 200 is placed within the aperture 204 and positioned to be coplanar with the second portion 202. The first portion 200 is then attached to the fiber optic plate 212 and the second portion 202. As shown in the exemplary embodiment of FIG. 5, the first portion 200 is formed of the CMOS panel 216 having the desired shape to conform to the aperture 204 and an electronics unit 218 operably connected to the CMOS panel 216. The CMOS panel 216 is secured to the fiber optic plate 212 using an optically clear bonding agent to retain the resolution provided by the CMOS panel 216. Further, the aperture 204 may additionally include a portion 220 that extends below the a-Si panel 210 into the foam layer 106,124 in order to accommodate the CMOS panel electronics unit 218, which is in turn connected to the electronics layer 114. Also, the panel 108 may include a film layer (not shown) disposed over the co-planar a-Si panel 210 and the fiber optic plate 212 opposite the CMOS panel 216 to provide a moisture barrier and to secure a scintillator 214 to the hybrid panel 108 that is disposed over the a-Si panel 210 and CMOS panel 216 in an indirect imager panel 108, but which is not required to be present in a direct imager panel 108.

Once the CMOS panel 216 and electronics unit 218 forming the first portion 200 have been secured to the fiber optic plate 212 and foam layer 106 of the second portion 202, the hybrid panel 108 including the first portion 200 and the second portion 202 can be positioned on and/or connected to the support layer 112 and electronics layer 114 to form the detector 22.

Referring now to the illustrated exemplary embodiments of FIGS. 7A-7D, the first portion 200/CMOS panel 216 can have any desired shape, including square, circular, or any desired polygonal shape, such as those shown in FIGS. 6A-6D. Further, in other exemplary embodiment, the second portion 202 may not surround the entire perimeter of the first portion 200. For example, the second portion 202 can be formed to have a U-shape and the first portion 200 can be disposed between the opposed arms of the U-shape of the second portion 202.

Figure 8:
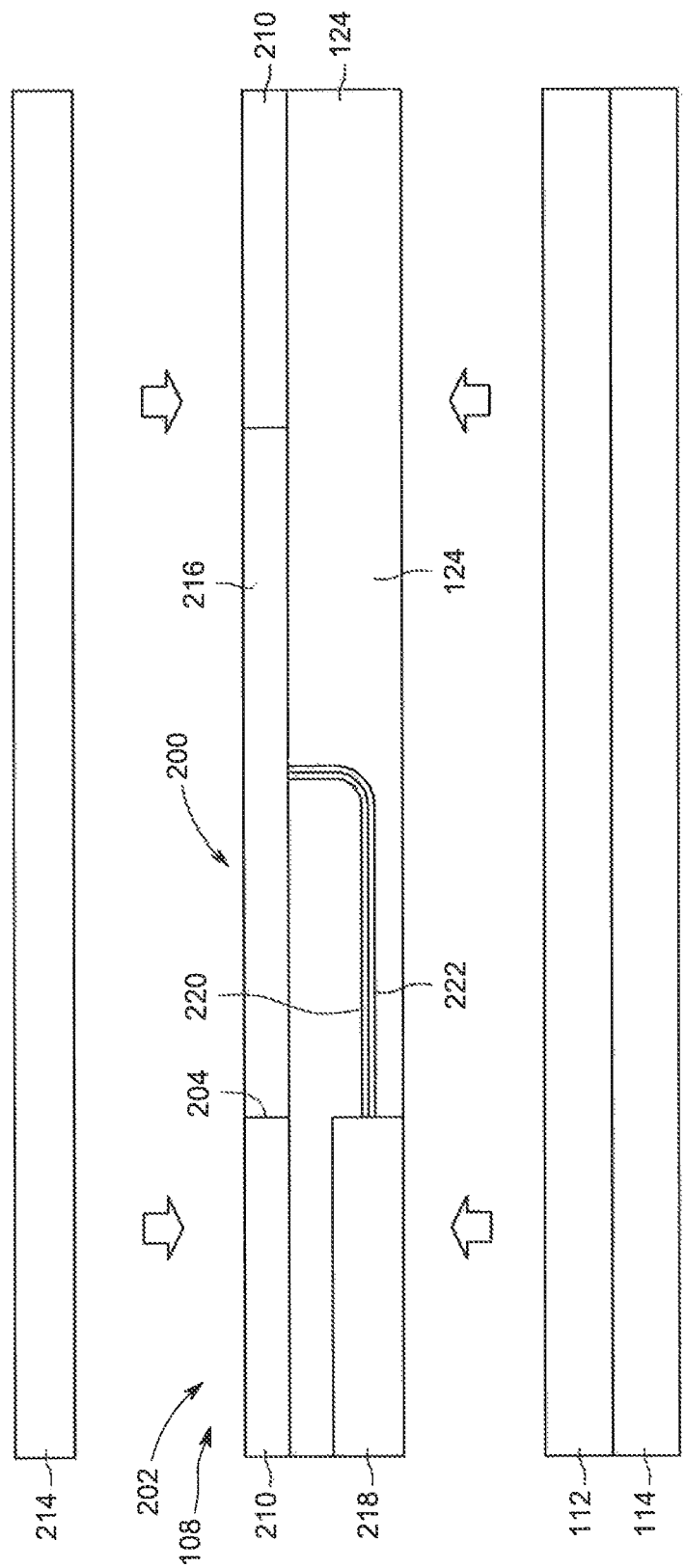
FIG. 8 is cross-sectional view of the hybrid imager panel constructed according to another exemplary non-limiting embodiment of the invention.

Looking now at the exemplary illustrated embodiment of FIG. 8, the construction of the hybrid panel 108 can be formed with the aperture 204 extending only through the a-Si panel 210. In this embodiment, a conduit or channel 220 is formed from the aperture 204 through the foam layer 106 and/or other layers of the detector 22 between the aperture 204 and the CMOS panel electronics 218. When the CMOS panel 216 of the first portion 200 is placed within the aperture 204 in the a-Si panel 210 such that the CMOS panel 216 is co-planar with the a-Si panel 210, a wire 222 or other conductor is threaded through the conduit 220 to connect the CMOS panel 216 to the electronics 218.

Figure 9:
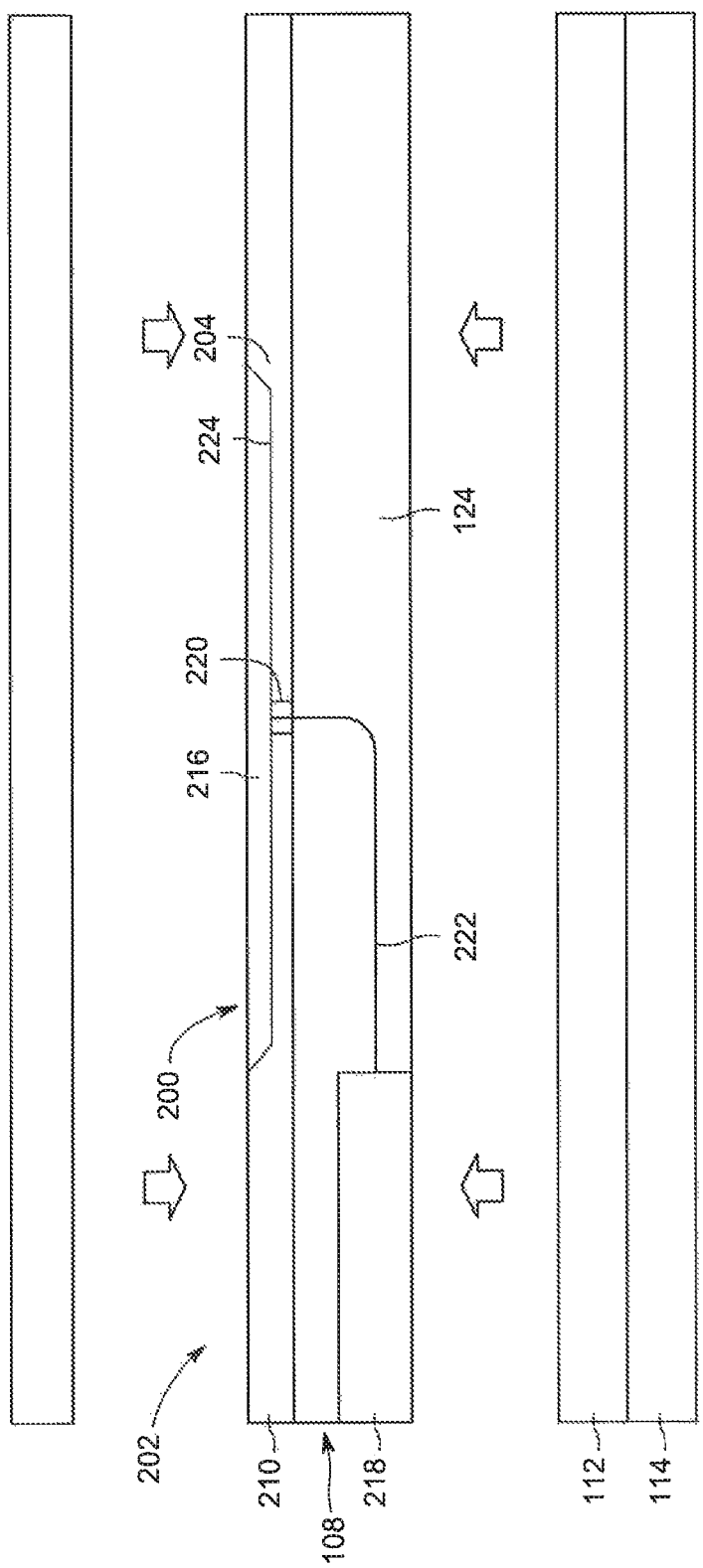
FIG. 9 is cross-sectional view of the hybrid imager panel constructed according to a further exemplary non-limiting embodiment of the invention.

Alternatively, as shown in the illustrated exemplary embodiment of FIG. 9, the aperture 204 can be formed to only partially extend through the a-Si panel 210. In this embodiment, the aperture 204 forms a recess 224 within the a-Si panel 210, which can be etched into the a-Si panel 201 or formed in any other suitable manner. The CMOS panel 216 of the first portion 200 can then be positioned within the recess 224 to be co-planar with the a-Si panel 210, with the connection 222 between the CMOS panel 216 and the electronics 218 being routed through the conduit 220.

In any of the embodiments of the hybrid panel 108 of this disclosure, the size of the pixels on the CMOS panel 216 can be adjusted relating to the position of the CMOS panel 216 relative to the a-Si panel 210. For example, when the CMOS panel 216 is disposed within the a-Si panel 210, as in the exemplary embodiments of FIGS. 7 and 8, the pixel size for the CMOS panel 216 can be adjusted to allow for binning of the pixels of the CMOS panel 216 to approximate the size of the pixels on the a-Si panel 210.

In operation, the presence of the first portion 200 and the second portion 202 enables the hybrid panel 108 to operate with different degrees of magnification that selectively employ the detection/resolution capabilities of the first portion 200 and second portion 202. In particular, the hybrid panel 108 can be operated in a first magnification configuration where the resolution corresponds to the pixel size/resolution of the a-Si panel 210, a second magnification configuration where the resolution corresponds to an interpolation of an image from the a-Si panel 210 with an image from the CMOS panel 216, and a third magnification configuration where the resolution corresponds to the pixel size/resolution for the CMOS panel 216.

In the first magnification configuration, to produce an image over the entire hybrid panel 108 adjacent pixels (not shown) in the CMOS panel 216 are grouped or binned with one another to form pixels approximating the size of the pixels of the a-Si panel 210, such that both the first portion 200 and the second portion 202 are being operated with the same or similar resolutions.

In the second magnification configuration, the images obtained by the first portion 200 and the second portion 202 are interpolated with one another to form a combine image with a higher resolution than that of the a-Si panel 210, but less than that of the CMOS panel 216 in the center of the image.

In the third magnification configuration, the image provided by the hybrid panel 108 is focused on the first portion 200 and the high resolution image provided by the native pixels of the CMOS panel 216.

Thus, with the combination of the first portion 200 and the second portion 202 in the hybrid panel 108, the detector 22 can be selectively operated to provide images having the desired resolution of the object being imaged by configuring the first portion 200 to provide image data that corresponds to the image data/pixel size of the second portion 202, that can be combined with the image data/pixel size of the second portion 202, or that can be utilized separately from the image data/pixel size of the second portion 202 to provide the image with the desired resolution.

Further, apart from or in conjunction with the resolution, the first portion 200 and the second portion 202 can be operated with varying frame rates to achieve the desired images from the imager panel 108.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A hybrid imager panel for an x-ray detector, the panel comprising:
    a first portion including a first imaging panel formed of a first X-ray imaging material having a first image resolution; and
    a second portion at least partially surrounding the first portion and including a second imaging panel formed of a second X-ray imaging material having a second image resolution, wherein the first image resolution is different that the second image resolution.

2. The hybrid imager panel of claim 1, wherein the first image resolution is higher than the second image resolution.

3. The hybrid imager panel of claim 1, wherein the first portion is disposed at the center of the hybrid imager panel.

4. The hybrid imager panel of claim 1, wherein the first imaging panel material is complementary metal oxide semiconductor (CMOS) imaging panel material.

5. The hybrid imager panel of claim 1, wherein the second imaging panel material is an amorphous silicon (a-Si) imaging panel material.

6. The hybrid imager panel of claim 1, wherein the second portion includes an aperture in which the first imaging panel is positioned.

7. The hybrid imager panel of claim 6, wherein the aperture extends only partially through the second portion.

8. The hybrid imager panel of claim 7, further comprising a conduit extending through the second portion between the aperture and a surface of the second portion opposite the aperture.

9. The hybrid imager panel of claim 6, wherein the aperture extends completely through the second portion.

10. The hybrid imager panel of claim 9, further comprising a fiber optic plate disposed within the aperture, wherein the first imaging panel is secured to the fiber optic plate.

11. A detector for use in conjunction with an X-ray imaging system, the detector comprising:
    an enclosure;
    a hybrid imager panel disposed within the enclosure, the hybrid imager panel comprising:
        a second imaging panel formed of a second X-ray imaging material and including an aperture in the second imaging panel; and
        a first imaging panel formed of a first X-ray imaging material and disposed at least partially within the aperture, wherein the first material is different than the second material; and
        an electronics layer operably connected to the first portion and the second portion of the hybrid imager panel.

12. The detector of claim 11, wherein the second imaging panel includes an aperture in which the first imaging panel is positioned.

13. The detector of claim 11, wherein the first image resolution is higher than the second image resolution.

14. The detector of claim 11, wherein the first imaging panel is disposed at the center of the hybrid imager panel.

15. A method for forming a hybrid imager panel for a detector for use in conjunction with an X-ray imaging system, the method comprising:
    forming a second imaging panel formed of a second X-ray imaging material;
    forming an aperture in the second imaging panel; and
    positioning a first imaging panel formed of a first X-ray imaging material at least partially within the aperture, wherein the first material is different than the second material.

16. The method of claim 15, wherein the step of forming the aperture comprises forming the aperture completely through the second imaging panel.

17. The method of claim 15, wherein the step of forming the aperture comprises forming the aperture partially through the second imaging panel.

18. The method of claim 15 wherein the first material is a complementary metal oxide semiconductor material.

19. A method of operating a detector for use in conjunction with an X-ray imaging system including a hybrid imager panel; the method comprising:
    providing the detector including the hybrid imager panel having a first portion including a first imaging panel formed of a first X-ray imaging material having a first image resolution and a second portion at least partially surrounding the first portion and including a second imaging panel formed of a second X-ray imaging material having a second image resolution, wherein the first image resolution is different that the second image resolution;

selecting a magnification configuration for the hybrid imager panel; and operating the hybrid imager panel in the selected magnification configuration.

20. The method of claim 19, wherein the step of selecting a magnification configuration comprises selecting one of a first magnification configuration where the resolution corresponds to the resolution of the second imaging panel, a second magnification configuration where the resolution corresponds to an interpolation of image data of the second imaging panel with image data from the first imaging panel, and a third magnification configuration where the resolution corresponds to the pixel resolution for the first imaging panel.

* * * * *